United States Patent
Prosser

(10) Patent No.: US 7,825,392 B2
(45) Date of Patent: Nov. 2, 2010

(54) CLEANING PROCESS FOR RADIOPHARMACEUTICAL REUSABLE PIGS

(76) Inventor: Rodney Wayne Prosser, 8A Hemlock Rd., Columbia, NJ (US) 07832

(*) Notice: Subject to any disclaimer, the term of this patent is extended or adjusted under 35 U.S.C. 154(b) by 279 days.

(21) Appl. No.: 12/248,017

(22) Filed: Oct. 8, 2008

(65) Prior Publication Data
US 2010/0084585 A1    Apr. 8, 2010

(51) Int. Cl.
G21F 5/00    (2006.01)
A61N 5/00    (2006.01)

(52) U.S. Cl. .................................. 250/506.1; 250/507.1

(58) Field of Classification Search .............. 250/506.1, 250/507.1
See application file for complete search history.

(56) References Cited

U.S. PATENT DOCUMENTS

| | | | | |
|---|---|---|---|---|
| RE36,693 E * | 5/2000 | Reich | ........................ | 250/507.1 |
| 6,425,174 B1 * | 7/2002 | Reich | ........................ | 29/469 |
| 6,544,193 B2 * | 4/2003 | Abreu | ........................ | 600/558 |
| 6,576,918 B1 * | 6/2003 | Fu et al. | ........................ | 250/507.1 |
| 6,722,499 B2 * | 4/2004 | Reich | ........................ | 206/365 |
| 7,019,317 B1 * | 3/2006 | Martin et al. | ........................ | 250/506.1 |
| 7,040,856 B2 * | 5/2006 | Reich | ........................ | 414/810 |
| 7,086,133 B2 * | 8/2006 | Reich | ........................ | 29/426.3 |
| 7,268,359 B2 * | 9/2007 | Fu et al. | ........................ | 250/507.1 |
| 7,495,246 B2 * | 2/2009 | Fago et al. | ........................ | 250/506.1 |
| 7,692,173 B2 * | 4/2010 | Fago et al. | ........................ | 250/506.1 |
| 2002/0165218 A1 * | 11/2002 | Halbrook et al. | ........................ | 514/210.2 |
| 2007/0034537 A1 * | 2/2007 | Fago et al. | ........................ | 206/364 |
| 2007/0084474 A1 * | 4/2007 | Rivard | ........................ | 128/898 |
| 2008/0200747 A1 * | 8/2008 | Wagner et al. | ........................ | 600/5 |
| 2010/0084585 A1 * | 4/2010 | Prosser | ........................ | 250/507.1 |

OTHER PUBLICATIONS

Pickett et al., The Incidence of Blood Contamination of Lead Unit Dose Containers With and Without Single-Use Protective Inserts Used with Commercially Prepared Readiopharmaceutical Unit Doses, Journal of Nuclear Medicine Technology, vol. 26, No. 3, Sep. 1998.

Taurasi, Sufficient sanitization, disinfection levels and wet sterile packages, Highbeam Encyclopedia, Healthcare Purchasing News, Aug. 1, 2002.

* cited by examiner

*Primary Examiner*—David A Vanore
(74) *Attorney, Agent, or Firm*—Arthur L. Lessler

(57) ABSTRACT

A process for cleaning containers (pigs) in which radioactive drugs are shipped to health care providers, after than are returned to a pharmacy and may contain residual radioactive material, blood, microorganisms and other contaminants. Those pigs that are contaminated with radioactive material are removed from the cleaning process until they have decayed to the background radiation level. The upper and lower portions of each blood contaminated pig is disinfected. Each pig is washed at a temperature of at least 180° Fahrenheit for a least one minute to kill bacteria and viruses. The combination of a disinfectant and high washing temperature water provides an optimum level of sterilization.

11 Claims, 3 Drawing Sheets

Figure 2:
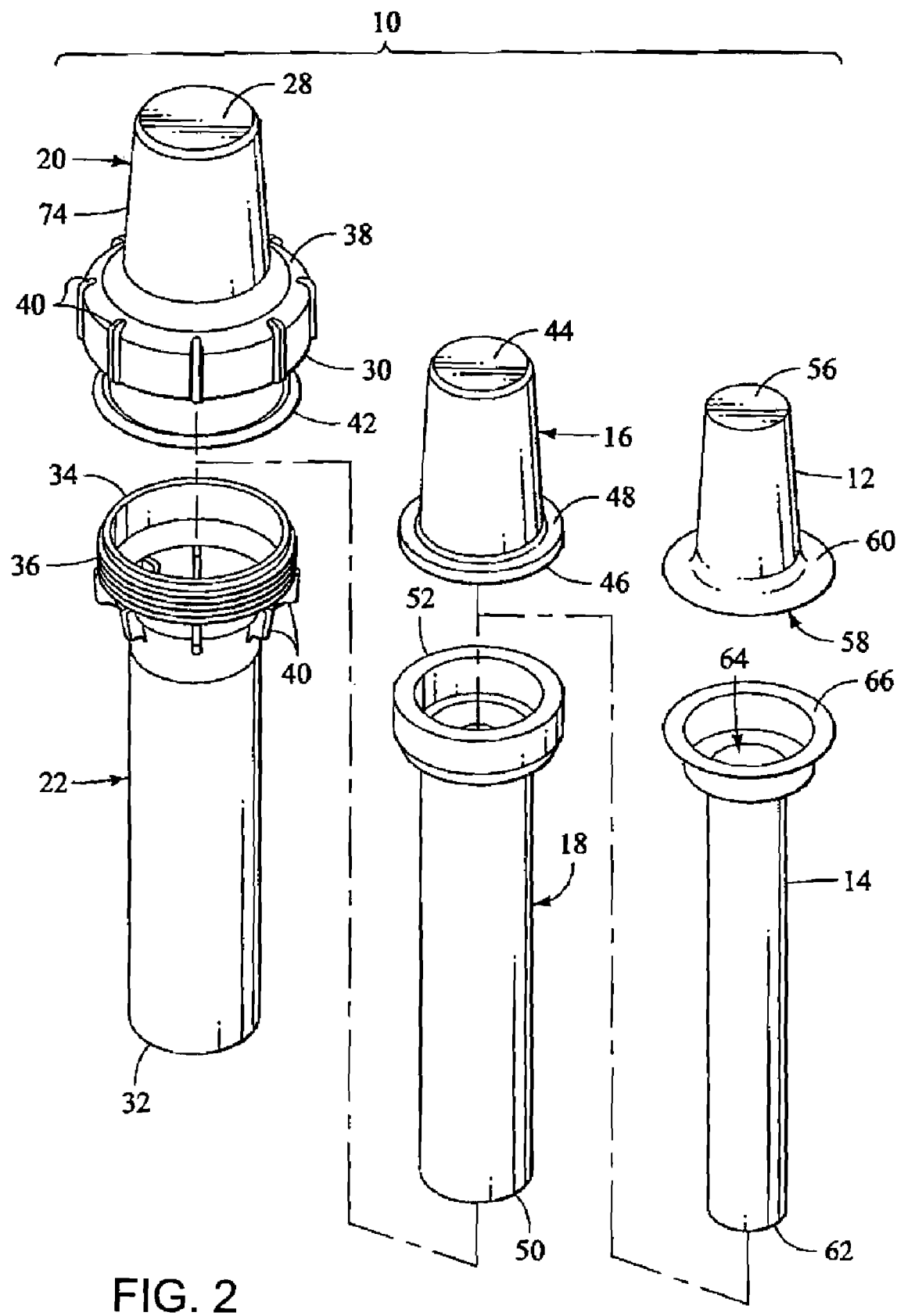

Step 1
Return pigs containing spent radioactive doses in a transport box.

Step 2
Remove pigs from the transport boxes. Survey transport boxes and their contents with Geiger counter or scintillation detector to insure all the radioactive material is contained in the pigs.

Step 3
Store contaminated radioactive boxes and contaminated contents until radioactivity decays to background level.

Step 4
Disassemble pigs and empty contents into a radiation attenuating containment vessel.

Step 5
Identify pigs that are contaminated with radioactive material and store them until radioactivity decays to background level.

Step 6
Inspect radioactivity-free pigs for visual evidence of blood contamination and disinfect contaminated ones.

Step 7
Internally inspect each pig for radioactive contamination utilizing a high sensitivity detection system (NaI photomultiplier tube probe attached to a scaler, ratemeter, or survey meter). This device has to be more sensitive then a Geiger-Müller probe attached to a survey meter.

Step 8
Immerse pig in disinfectant.

Step 9
Wash pig at temperature of at least 180° Fahrenheit and dry same.

Fig. 1

CLEANING PROCESS FOR RADIOPHARMACEUTICAL REUSABLE PIGS

BACKGROUND OF THE INVENTION

This invention relates to a process for cleaning radiopharmaceutical reusable shipping containers which are generally referred to as pigs; and more particularly for cleaning pigs utilized for shipping radioactive drugs having relative short half lives, typically on the order of no more than a few days.

Radioactive drugs are typically shipped by pharmacies to hospitals, clinics and medical offices, frequently for diagnostic purposes. The drugs are shipped in pigs, each of which has a lead surround for radiation shielding and contains an inner chamber that may contain a syringe or vial which is suitable for dispensing an individual dose of a radioactive labeled drug.

The radiopharmaceutical pig typically is a two-part assembly, with an upper portion removably attached to the lower portion. The assembled pig includes a sealed internal chamber comprising a syringe containment enclosure suitable for carrying a syringe, and a lead radiation shield surrounding the chamber. The shield may be surrounded by an exterior plastic protective shell.

When a prescription is to be filled, a syringe or vial is placed in the lower portion of the syringe containment enclosure of the pig and the pig is assembled by threading the upper portion to the lower portion.

At the hospital or other medical facility, the pig is disassembled and the syringe is removed. After the dose is injected into the patient, the syringe usually contains a small amount of residual radioactive drug and is biologically contaminated, usually with blood, from coming into contact with the patient. It is put back in the bottom portion of the pig, and the spent pig is assembled and sent back to the pharmacy.

The spent pig is not suitable for reuse until any blood, microorganisms and residual radiation, and any other contaminants have been removed. The combination of radioactive material with other contaminants makes the cleaning of the returned pigs very difficult.

A prior art method for cleaning the spent pigs consists of the following steps:

The pigs are returned to the pharmacy in transport boxes.
The boxes and their internal contents are surveyed for radioactivity using a Geiger-Muller survey meter.
Radioactivity contaminated boxes and pigs are removed and stored until the radioactivity has decayed to background level.
The residual contents of the pigs are dumped into a lead or other radiation attenuating barrel.
The pigs are checked with a Geiger-Muller survey meter for radioactivity contamination and visually inspected for the presence of blood.
Pigs contaminated with blood are treated in a 10% solution of bleach in water.
The pig is then reused by placing a new syringe or vial containing a radioactive drug ordered by a customer within each pig which has not been found to be contaminated, and the pig is sent to the customer.

Unfortunately pigs which have been cleaned by this process have a relatively high incidence of contamination, indicating that the prior art cleaning process needs improvement.

Another prior art solution to the pig cleaning problem has been to utilize a disposable insert that fits into the cavity of the pig, with the syringe being disposed within the insert. Such an arrangement is shown in U.S. Pat. No. 7,268,359 to Fu et al., FIGS. 1 and 2 of which appear as FIGS. 2 and 3 of the present application respectively—so that the numbered elements of these figures are as described in the Fu et al. patent. The disclosure of U.S. Pat. No. 7,268,359 is hereby incorporated into the present application.

Figure 3:
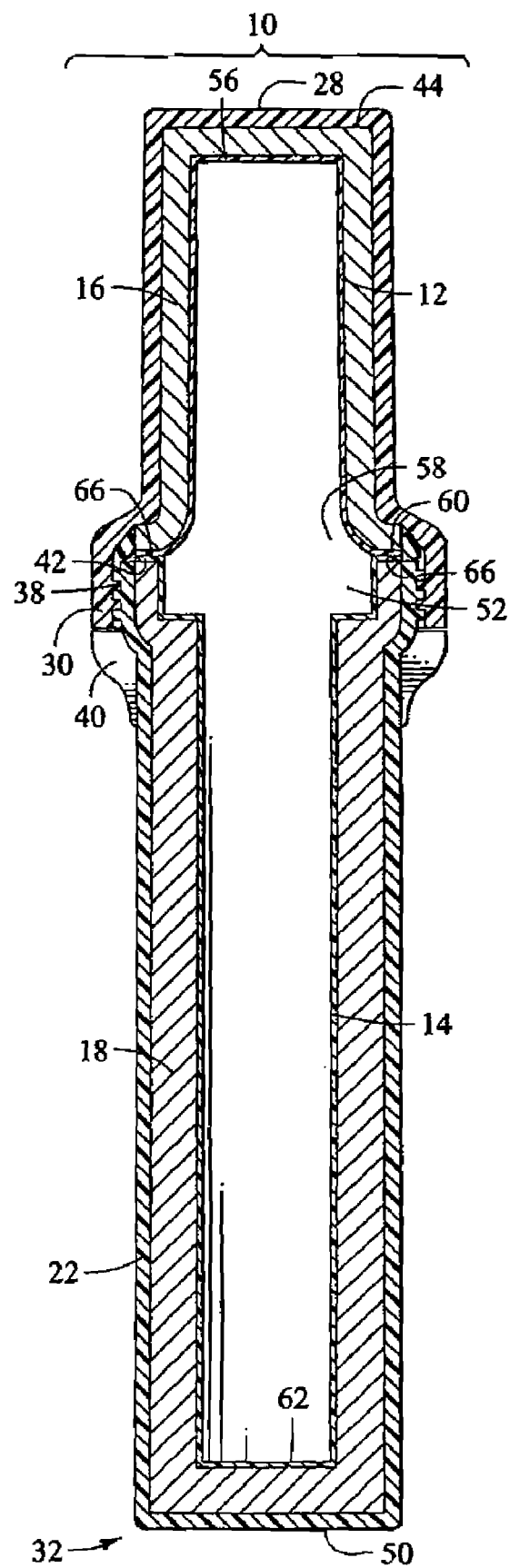

As seen in FIGS. 2 and 3, the disposable insert of Fu et al. comprises an upper lining 12 and a lower lining 14 which nest together to form a chamber for a syringe which is placed in the lower lining 14; the insert being placed in the chamber formed by the upper radiation shield portion 16 and the lower radiation shield portion 18.

However, the insert system of Fu et al. does not provide a perfect seal and does not completely remove contaminants. In a study by Pickett et al. entitled The Incidence of Blood Contamination of Lead Unit Dose Containers With and Without Single-Use Protective Inserts Used with Commercially Prepared Radiopharmaceutical Unit Doses, Journal of Nuclear Medicine Technology, Volume 26, No. 3, Sept. 1998, 1% of the pigs utilizing inserts arrived at the nuclear medicine department with detectable blood contamination. A substantially lower contamination level is desirable. Moreover, the insert system does not address bacterial, viral, blood, radioactive and other contaminants that exist on the outside of the pigs. Consequently, subsequent doses of radiopharmaceuticals may be distributed in pigs that are contaminated with biological and/or radioactive contaminants.

Accordingly, an object of the present invention is to provide a process for cleaning radiopharmaceutical pigs that may or may not have disposable inserts.

SUMMARY OF THE INVENTION

As described herein, a process is provided for cleaning a radiopharmaceutical reusable pig by scanning the pig externally and internally to detect the presence of radioactivity at a radiation level above background level, and if such radiation is detected storing the pig until the radiation has decayed to background level. The pig is then disinfected, washed at a high enough temperature and for a long enough time to destroy microorganisms and remove blood contamination.

IN THE DRAWING

FIG. 1 is a diagram showing the steps in a preferred embodiment of the process of the invention;

FIG. 2 is a pig having a disposable insert according to the prior art as shown in U.S. Pat. No. 7,268,359; and FIG. 3 is an elevation cross-sectional view of the pig shown in FIG. 2.

DETAILED DESCRIPTION

The process described herein includes operations to insure that after cleaning, the pigs are free of contaminants of all kinds mentioned above; and provides pigs that are clean inside and outside and suitable for reuse.

Referring to FIG. 1, the spent pigs containing used syringes and vials are returned to the pharmacy in federal Department of Transportation approved transport boxes (Step 1). At Step 2 the pigs are removed from the transport boxes which are then surveyed, that is scanned with a radiation detector such as a Geiger counter or a scintillation detector. At Step 3 Boxes emitting radiation above the environmental background level are stored until radioactive decay eliminates the radiation so that the detected level is only the background level.

For example, since a commonly used radioactive substance (Technetium 99) has a half life of only six hours, three or four days of storage is usually enough for any radiation from a box which contained a pig that delivered this substance to decay to the background level.

Alternatively, the transport boxes may be scanned while the pigs are in them, since the shielding of the pigs will prevent any significant amount of radiation from emanating from the material within the pigs.

At Step 4 each pig is disassembled by unscrewing the upper portion from the lower portion, and the contents (syringe or vial) is dumped into a radiation attenuating containment vessel such as a covered lead receptacle.

At Step 5 a Geiger counter is used to identify pigs that are contaminated with radioactive material. These contaminated pigs are pulled from the process and held in storage until the radiation has decayed to the background level, which means that the pigs are free of radioactivity. The Geiger counter is positioned near the upper and lower portion of each pig and thus measures external radiation generated by radioactive material on the inner and outer surface of the pig.

At Step 6 pigs which are externally free of radioactivity, that is, which do not show any above-background radioactivity on the Geiger counter, are visually inspected for evidence of blood. If any visual signs of blood are present the pig is pulled from the process and it is disinfected at Step 8 by exposure to an appropriate disinfectant chemical. Alternatively, but less preferably, the pigs may be inspected and disinfected before they are checked for radioactivity. In this altered sequence the decontamination liquid will become radioactive and the liquid will have to be handled as radioactive waste. This can create a waste storage problem.

At Step 7 each pig is internally checked for radioactivity using a highly sensitive probe such as that of a NaI probe coupled to a Geiger or Geiger-Muller counter (survey meter) or scintillation detector (SCA Scaler/Ratemeter), the NaI photomultiplier tube probe being more sensitive than a Geiger counter (survey meter) which is the current standard in the industry. This is done by passing the probe near the cavity in the lower portion of the pig, that is, as close as possible to the mouth of the lower shell 22 and the mouth of the lower radiation shield 18.

The NaI probe has to be in close proximity (no more than one inch and preferably less than 0.1 inch) to the mouth of the cavity of the pig. If the background radiation of the room in which the checking is done is not low enough the probe will require additional shielding. An alternate method of detection is to utilize a probe that will fit down inside of the cavity of the pig.

Any pig exhibiting radioactivity readings above background level is pulled from the process and held in storage until the radiation has decayed to the background level, after which the pig is returned to the cleaning process.

The syringe containment enclosure comprises the upper radiation shield 16 and the lower radiation shield 18. Currently, pharmacies use a Geiger-Muller probe attached to a survey meter to identify radioactive contamination that is on pigs that are returned to the pharmacies. However, this method is not sensitive enough to detect small amounts of radiation that may reside in the bottom portion of the container 18. This radioactive material will be removed during the wash process and it contaminates the wash water and the washing machine and disperses the contamination to the outside of the containers. This contamination will then cross contaminate onto the hands of the individuals who unload the washing machine.

If desired or if there is reason to suspect leakage of material into them, the upper portion 16 of the radiation shield and the upper and lower portions 20 and 22 of the shell which encases the shield may also be checked for radioactivity by the high sensitivity NaI scintillation detector (photomultiplier) probe.

At Step 8 both portions of the pigs, which are then free of radioactivity and visible blood contamination, are dipped in a disinfectant water bath. Then the pigs are washed in a washing machine at a temperature of at least 180° Fahrenheit, and preferably of at least 205° Fahrenheit for at least one minute to provide an additional, intermediate, level of disinfection as pointed out in an article by Ray Taurasi entitled Sufficient sanitization, disinfection levels and wet sterile packages (CS Questions, CS Answers), Highbeam Encyclopedia, from Healthcare Purchasing News, Aug. 1, 2002. Thereafter the pigs are allowed to air dry, with or without fan circulation of air.

The disinfecting solution (for Step 8) can be incorporated into the washing cycle if the washing machine has a pump attachment that adds the disinfectant to the wash cycle.

While the aforementioned steps have been described in a particular sequence, the sequence of steps may be altered, so long as radiation is removed from the pigs before they are disinfected and washed. The transport boxes may be scanned for radioactivity at any desired time.

I claim:

1. A process for cleaning one or more spent radiopharmaceutical reusable pigs held in a transport box, each pig having a syringe or vial containment enclosure, comprising the steps of:

removing each pig from the transport box;

after removing all pigs from the transport box, scanning the box to detect the presence of radioactivity at a radiation level above background level;

upon detecting the presence of transport box radioactivity at said radiation level, storing the radioactive box until the radiation has decayed to background level;

disassembling each pig and emptying the contents thereof into a radiation attenuating containment vessel;

scanning each disassembled pig externally to detect the presence of radioactivity at a radiation level above background level;

upon detecting the presence of radioactive contamination of the pig at said radiation level, storing the radioactive pig until the radiation has decayed to background level;

scanning at least the lower portion of the syringe or vial containment enclosure of each pig utilizing a high sensitivity probe adjacent said lower portion to detect the presence of radioactivity emanating from inside the pig at a radiation level above background level;

upon detecting the presence of emanating radioactivity at said radiation level, storing the radioactive pig until the radiation has decayed to background level;

inspecting the pigs exhibiting radiation at background level for evidence of blood contamination;

disinfecting the spent pigs; and washing all the pigs at a temperature of at least 180° Fahrenheit for at least one minute.

2. The process according to claim 1, wherein said probe is substantially more sensitive than a Geiger-Muller probe attached to a survey meter.

3. The process according to claim 1, wherein said probe is an NaI probe.

4. A process for cleaning a spent radiopharmaceutical reusable pig having a syringe or vial containment enclosure, comprising the steps of:

scanning the pig externally to detect the presence of radioactivity at a radiation level above background level;

upon detecting the presence of external pig radioactivity at said radiation level, storing the radioactive pig until the radiation has decayed to background level;

thereafter disassembling the pig and emptying the contents thereof into a radiation attenuating containment vessel;

scanning at least the syringe or vial containment enclosure of the disassembled pig utilizing a high sensitivity probe adjacent the enclosure to detect the presence of radioactivity inside the pig at a radiation level above background level;

upon detecting the presence of pig radioactivity emanating from said enclosure at said radiation level, storing the radioactive pig until the radiation has decayed to background level;

inspecting the pig exhibiting radiation at background level for evidence of blood contamination;

disinfecting the pig by exposing it to a disinfectant chemical; and washing the pig.

5. The process according to claim 4, wherein said washing step is carried out at a temperature of at least 180° Fahrenheit for at least one minute.

6. The process according to claim 4, wherein said probe is connected to a scintillation detector.

7. The process according to claim 4, wherein said probe is capable of detecting radioactivity emanating from within the shield of the pig.

8. A process for cleaning a radiopharmaceutical reusable pig having a syringe or vial containment enclosure, comprising the steps of:

scanning the pig externally and at least the lower portion of the syringe containment enclosure internally to detect the presence of radioactivity at a radiation level above background level;

upon detecting the presence of radioactivity at said radiation level, causing said pig to cease exhibiting said radioactivity;

disinfecting the pig; and washing the disinfected pig at a temperature of at least 180° Fahrenheit for at least one minute.

9. The process according to claim 8, wherein said pig is caused to cease exhibiting said radioactivity by storing the radioactive pig until the radiation has decayed to background level as determined by a high sensitivity radioactivity detection device.

10. The process according to claim 9, wherein said radioactivity detection device includes a photomultiplier tube.

11. A process for cleaning a radiopharmaceutical reusable pig having a syringe or vial containment enclosure, comprising the steps of:

scanning the pig externally and at least the lower portion of the syringe containment enclosure internally to detect the presence of radioactivity at a radiation level above background level;

upon detecting the presence of radioactivity at said radiation level, causing said pig to cease exhibiting said radioactivity; and washing the pig at a sufficiently high temperature for a sufficiently long time to destroy any microorganisms and remove any blood contamination from said pig.

* * * * *